United States Patent [19]

Inahara et al.

[11] Patent Number: 4,903,322
[45] Date of Patent: Feb. 20, 1990

[54] APPARATUS FOR MANAGING CHANNELS OF RADIO COMMUNICATION SYSTEM

[75] Inventors: Kazuo Inahara, Saitama; Junichi Igarashi, Tokyo, both of Japan

[73] Assignee: Nihon Kohden Corporation, Tokyo, Japan

[21] Appl. No.: 158,348

[22] Filed: Feb. 22, 1988

[30] Foreign Application Priority Data

Feb. 23, 1987 [JP] Japan .................................. 62-39944

[51] Int. Cl.$^4$ ............................................... H04Q 7/00
[52] U.S. Cl. ........................................ 455/34; 455/56; 455/186
[58] Field of Search ............... 455/186, 185, 187, 188, 455/54, 56, 34, 70, 71, 58; 340/825.03, 825.07, 825.15

[56] References Cited

U.S. PATENT DOCUMENTS 4,545,071 10/1985 Freeburg ............................... 455/56
4,573,206 2/1986 Gravel et al. ......................... 455/34

*Primary Examiner*—Joseph A. Orsino
*Assistant Examiner*—Frank M. Scutch, III
*Attorney, Agent, or Firm*—Hoffmann & Baron

[57] ABSTRACT

A channel management apparatus provided for a plurality of master radio communication units which perform communication by selecting as desired one or more of a plurality of channels that are respectively assigned to a plurality of slave radio communication units. This apparatus is provided with a shared storage device which is capable of being set on each master unit and which contains items of data on registered channels which correspond to all of channels used by the master units, and a plurality of groups of devices incorporated in the master units. Each of the groups of devices includes: a setting device for manually setting the channels used by corresponding one of the master units; a display device for displaying the channels used by the master unit; a channel data processing device adapted to make the display device display data on the registered channels by reading this data from the storage device which has been set, the data processing device updating the data on the registered channels in the storage device in accordance with the data on the channels used by the master unit supplied from the setting means; and a channel selecting device adapted to select, in accordance with the data on the channels to be used, channels through which the communication is performed.

4 Claims, 3 Drawing Sheets

APPARATUS FOR MANAGING CHANNELS OF RADIO COMMUNICATION SYSTEM

BACKGROUND OF THE INVENTION

This invention relates to an apparatus which manages channels of a radio communication system in a limited region or institution and which enables each of a plurality of master radio communication units to perform communication with a plurality of slave units by selecting desired radio channels of the radio channels specifically assigned to those slave units.

If radio communication is performed by a plurality of slave units and a plurality of master units in charge of the operation of respective slave units, then the management of radio channels is very important in order to avoid duplicated use of radio channels.

In a conventional method of radio channel management, a determination of which channels are in use and which are free is made by a man or computer through a separate medium, and this operation is not linked with master units. As a result, even if the channels selected to be used have been correctly registered, there is a strong possibility of prohibited channels being used, therefore causing problems such as radio interference.

SUMMARY OF THE INVENTION

It is therefore an object of the present invention to provide a channel management apparatus which improves the reliability of the channel management in a radio communication system in which uni-directional or bidirectional data communication is performed between a plurality of slave radio communication units to which channels are assigned and a plurality of master radio communication units which select the radio channels as desired.

To this end, the present invention provides a channel management apparatus which is provided for a plurality of master radio communication units that perform communication by selecting as desired, one or more of a plurality of channels that are respectively assigned to a plurality of slave radio communication units. The channel management apparatus includes a shared memory storage device which is capable of being set on each master unit and which contains items of data on registered channels which correspond to all of channels used by the master units. A plurality of groups of devices incorporated in the master units are provided. Each of the groups of devices include: a setting device for manually setting the channels used by corresponding one of the master units; a display device for displaying the channels used by the master unit as usable or unusable channels; a channel data processing device adapted to make the display device display data on the registered channels by reading this data from the memory storage device which has been set, with the data processing device updating the data on the registered channels in the storage device; and a channel selecting device adapted to select, in accordance with the data on the channels to be used, channels through which the radio communication is to be performed.

In accordance with the present invention, when radio communication is performed by a plurality of master units in charge of the operation of respective slave units, the provision of the shared data storage device facilitates the management of channel assignment to the master units, thereby preventing problems such as radio interference.

The above and other objects, features, and advantages of the present invention will become more apparent from the following description when taken in conjunction with the accompanying drawings in which a preferred embodiment of the present invention is shown by way of illustrative example.

DESCRIPTION OF THE PREFERRED EMBODIMENT

Figure 1:
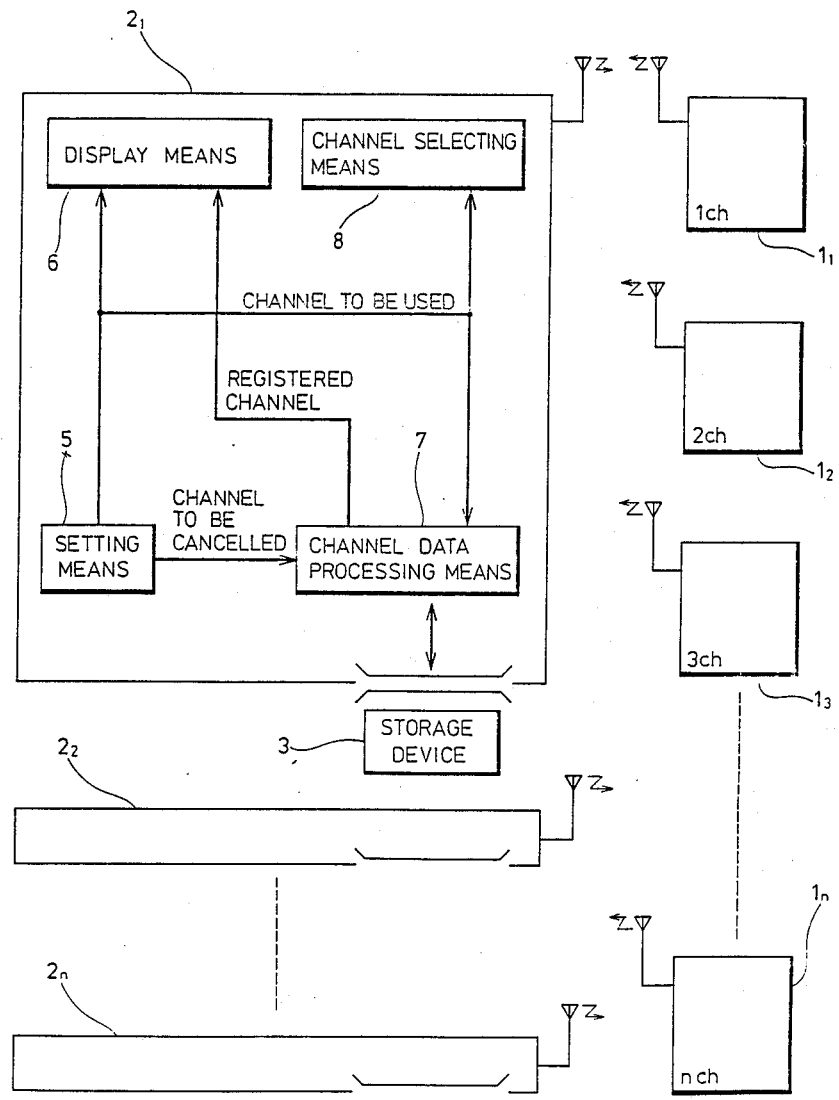
FIG. 1 is a circuit block diagram of a channel observation apparatus which has a constitution based on the principles of the present invention.

Referring to FIG. 1, radio channel management apparatus of the present invention is shown. Such apparatus is used in connection with a plurality of master radio communication units $2_l$ to $2_m$ which perform communication by selecting one or more of a plurality of channels "chl" to "chn" that are assigned to a plurality of slave radio communication units $1_l$ to $1_n$, respectively. The components of the channel management apparatus of the present invention will be described hereinbelow.

A shared memory storage device 3 which is capable of being set on the master units $2_l$ to $2_m$ and which is constituted by an EEPROM, floppy disk, etc., is provided. The EEPROM contains items of data on registered channels which correspond to channels used by the master units $2_1$ to $2_m$. Each of the master units $2_l$ to $2_m$ is provided with a setting means 5, a display means 6, a data processing means 7, and a channel selecting means 8.

The setting means 5 is for manually setting channels which are used by that master unit and channels which are to be canceled. The display means 6 is adapted to display usable channels or unusable channels and the set channels used by this master unit. The display means 6 can be constituted by a cathode ray tube, a numerical value indicator, recording paper, and other conventional well known display means. The data processing means 7 causes the display means 6 to display data on registered channels as usable or unusable channels by reading this data from the storage device 3 which has been set. The data processing means 7 updates the data on registered channels in the storage device 3 in accordance with set data on the channels used by this master unit, and similarly updates the data on registered channels in accordance with the data on channels to be canceled. The channel selecting means 8 operates to select, in response to the setting of channels which are to be used, those channels through which data communication is performed.

This system operates in the following manner. If the master unit $2_1$ is to be operated, the storage device 3 is set to this master unit. The channel data processing means 7 reads out data stored in the storage device 3 on registered channels relating to other operating master units, and causes the display means 6 to display the usable or unusable channels. That is, if channels which are in use have been stored as registered data, those channels are directly displayed as unusable channels or, after calculation, they are displayed as usable channels. If channels which are in use have been stored as registered data on usable channels after preliminary calculation, then they are directly displayed as usable channels.

If a channel which the master unit desires to use is set by the setting means 5 on the basis of the displayed channels, then it is displayed on the display means 6 for confirmation. In accordance with this setting, the channel selecting means 8 enables this master unit to communicate with the slave unit $1_l$ of the corresponding channel, and, at the same time, the channel data processing means 7 updates the registered data in the storage device 3 by erasing the data on usable channels in accordance with the data on the channels used by this master unit.

If a registered channel is to be canceled, the channel to be canceled (i.e., which will not be used) is set by the setting means 5 so that the channel selecting means 8 is stopped from selecting that channel while the channel data processing means 7 correspondingly updates the data in the storage device 3.

If another master unit $2_2$ is to be operated, channels used by this master unit are selected from remaining channels displayed on the display means 6 so as to enable communication while those selected channels are registered in the storage device 3.

Figure 2:
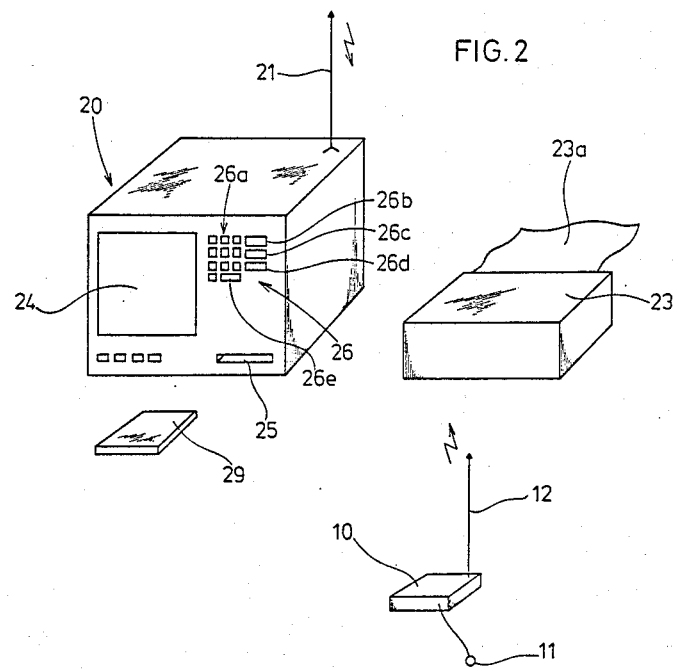
FIG. 2 is a perspective view of a radio communication unit in accordance with an embodiment of the present invention
Figure 3:
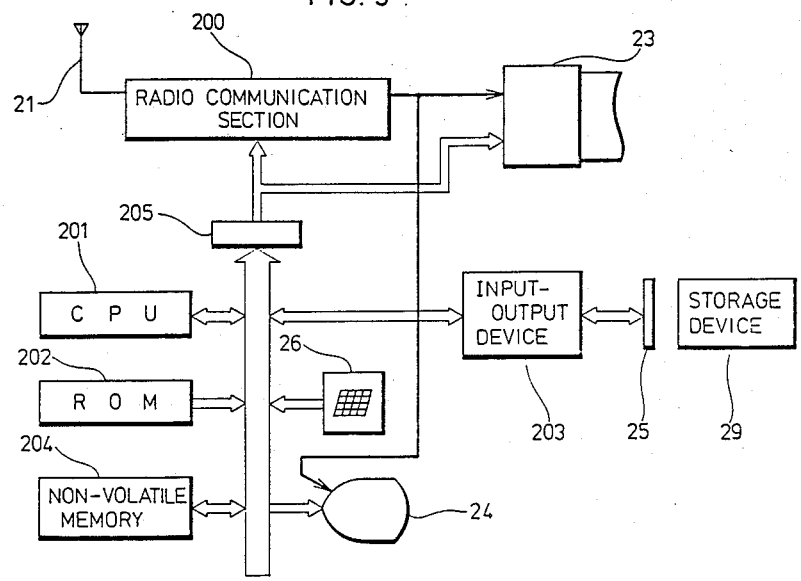
FIG. 3 is a circuit diagram of the embodiment relating to FIG. 2.

FIGS. 2 to 3 show an embodiment in which the present invention is applied to an electrocardiogram telemeter used in a hospital.

Referring to FIG. 2, 150 slave units 10, for example, are provided for use in a hospital. Each slave unit 10 is adapted to transmit an electrocardiographic signal induced through an electrode 11. Several dozen master units 20 are provided in the hospital. In each master unit 20, a receiving section selectively receives through an antenna 21 signals which are transmitted from slave units through 150 channels assigned to the slave units. A recorder 23 is attached to each master unit 20 by way of connector known is the art.

The panel of each master unit 20 is provided with a cathode ray tube 24, a slot 25 into which a storage device in the form of a card incorporating a floppy disk is removably set, and a keyboard 26. The keyboard 26 is provided as a setting means and includes a ten-key cluster 26a for setting channels, a registration key 26b, a cancellation key 26c, a confirmation key 26d, and an end key 26e. In the preferred embodiment, the recorder 23 and the cathode ray tube 24 are capable of recording or displaying electrocardiographic waveforms supplied through four channels.

FIG. 3 shows the circuit arrangement of the master unit 20. A radio communication section 200 receives from the antenna 21, four channels of electrocardiographic signals selected by a channel change-over circuit known in the art and incorporated in the receiving section 200. The outputs from the radio communication section 200 are detected waveform signals which are provided to the recorder 23 and the cathode ray tube 24. In accordance with a channel management program and stationary data stored in a ROM 202, a central processing unit (CPU) 201 is adapted to perform later-described data processing of data supplied from the data storage device 29 and through the keyboard 26. An input-output device 203, including a floppy disk deck provided with the slot 25 is adapted to conduct data exchange between the CPU 201 and the data storage device 29. A non-volatile memory 204 maintains (i) data on channels used by this master unit and (ii) the card number of the data storage device 29. Notably, nonvolatile memory 204 will retain such information even after the power to the unit has been terminated.

The CPU 201 operates in the following manner. First, the CPU reads data on the card number from the data storage device 29, compares this data with the corresponding data stored in the non-volatile memory 204, and sends, in the case of non-coincidence, non-coincidence data to the cathode ray tube 24 to display a registration-unable state. If the card number has not been registered, then the CPU stores it in the non-volatile memory 204. After the registration key 26b has been set, the CPU receives this key data, reads the data on registered channels stored in the data storage device 29, calculates usable channels from the data on all channels previously written in the ROM 202, and displays them on recording paper 23a of the recorder 23. When four channels to be used are set by the ten-key cluster 26a so that an item of key data is produced each time the end key 26e is operated, the CPU 201 successively sends items of data on the channels to be used, to the cathode ray tube 24, in response to the items of key data.

Thereafter, the CPU determines, in response to key data produced by the operation of confirmation key 26d, whether or not these channels overlap the registered channels, and displays for example "OK" or "NG" on the cathode ray tube 24. When the end key 26e is operated in the OK state, the CPU activates, in response to this function selection, the channel-change-over circuit incorporated in the radio communication section 200 so as to enable reception through the four set channels, and it registers through the input-output device 203, the data on channels to be used. If the cancellation key 26c is operated and if the data on registered channels have not been displayed, the CPU displays, on the cathode ray tube 24, this data, the data on the channels to be used read out from the non-volatile memory 204, and the data on a channel to be canceled which has been set by the ten-key cluster 26a and the end key 26e. Then, in response to the operation of the confirmation key 26d, the CPU determines whether or not the channel to be canceled is included in the channels to be used, thereafter displaying OK or NG. When the end key 26e is operated in response to OK, the CPU erases the data on the corresponding registered channel in the storage device 29 and the content of the non-volatile memory 204 and cancels the reception of the channel to be canceled.

Figure 4:
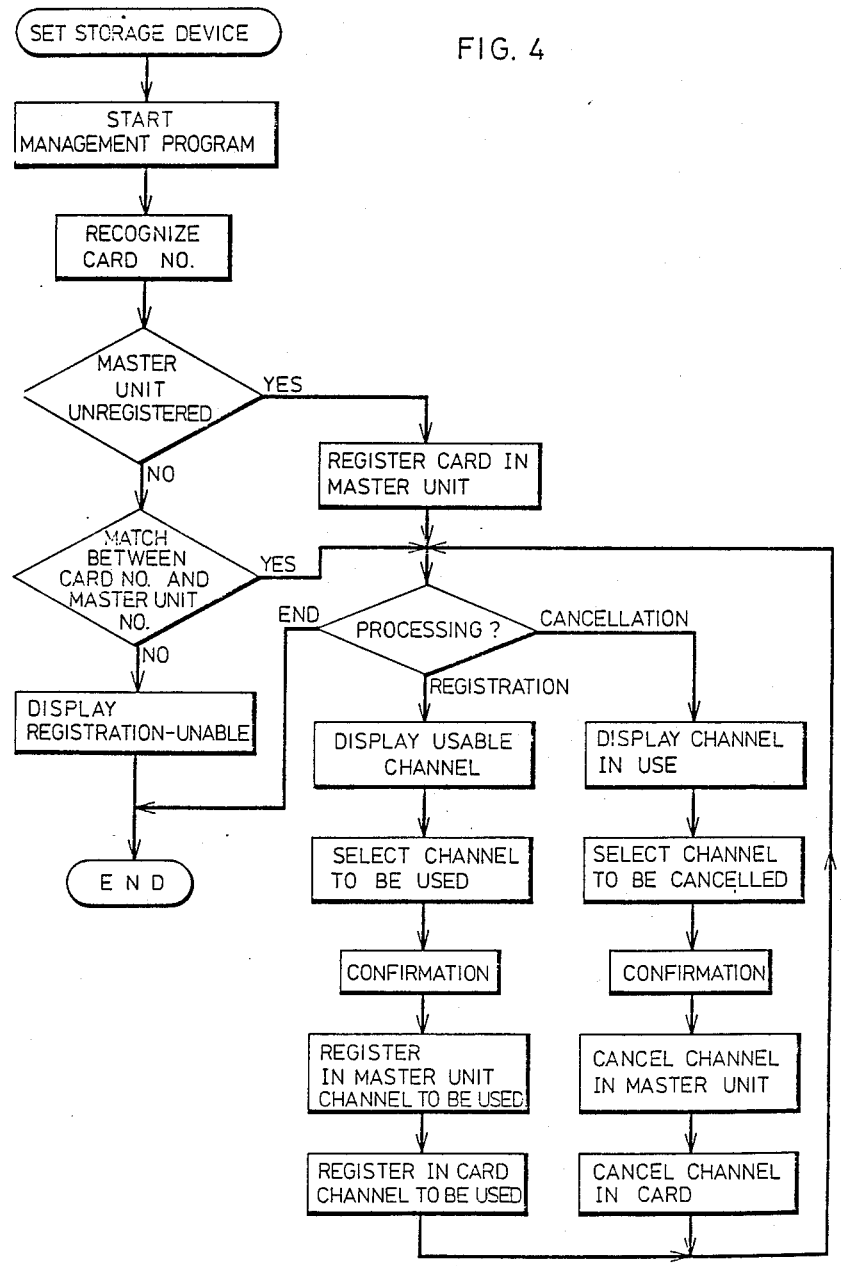
FIG. 4 is a flow chart of the operation in accordance with the embodiment of the present invention relating to FIG. 2.

The operation of the thus-constructed management apparatus will be described below with reference to the flow chart of FIG. 4.

If one of the master units 20 is to be newly operated, the data storage device 29 is inserted in the slot 25 of that master unit 20. The CPU 201 starts the management program, compares the card number with the registered card number, and displays on the cathode ray tube 24 the registration-enable state in the case of coincidence or the registration-unable state in the case of non-coincidence. If the card number has not been registered, the registration-enable state is displayed after the registration of the card number. When the operator operates the registration key 26b, the data on registered channels stored in the storage device 29 is displayed on the recording paper 23a. Of the usable channels displayed on the recording paper 23a, at most four channels which are used by this master unit are successively input through the ten-key cluster 26a and are displayed by the operation of the end key 26e. After the OK display has been effected by operating the confirmation key 26d, the end key 26e is operated, thereby causing the radio communication section 200 to select these channels while performing writing into the non-volatile memory 204 and the storage device 29.

To cancel the use of a channel which has already been registered, the cancellation key 26c is operated so as to display the channels which are in use, and the channel to be canceled is also displayed by operating the end key 26e. The confirmation key 26d is operated so as to confirm that this channel is not a channel included in the registered channels for other master units 20 but a channel used by this master unit only. If the OK display is effected, the end key 26e is operated, thereby interrupting the selecting operation of the radio communication section 200 and canceling registration in the storage device 29 and the non-volatile memory 204.

In accordance with the above-described embodiment, the unit number of each master unit may be stored in the ROM 202 and stored in the storage device 29 together with the data on the channels which are in use, thereby enabling indication of which master unit is using which channel. This method is particularly suitable for a master unit having no non-volatile memory 204 to store in memory the channels that this unit is allowed to use, when this unit is started again after cutting off the power supply. The present invention can also be applied to a radio communication system in which the master unit not only simply displays an electrocardiographic waveform but also incorporates an analyzer for analyzing the waveform or controls the slave unit. Alternatively, the present invention can be applied to a radio communication system in which the slave unit selects not only its discriminated channel but also selects a plurality of channels through which a plurality of biophysiological signals are transmitted in linked relationship with the discriminated channel. If the management apparatus is adapted to make a plurality of master units 20 receive signals from one slave unit 10, it is necessary to change the above-described program regarding the confirmation operation. It is also possible to display the unit number of a master unit by assigning a channel which is used by this master unit.

While the particular embodiment shown and discussed above has proven to be useful in many applications, further modifications of the present invention herein described will aim to persons skilled in the art to which the present invention pertains and all such modifications are deemed to be within the scope and spirit of the present invention defined by the appended claims.

What is claimed is:

1. A channel management apparatus for use in connection with a plurality of master radio communication units which perform communication with a plurality of slave radio communication units by selecting as desired one or more of a plurality of channels that are respectively pre-assigned to said plurality of slave radio communication units, said apparatus comprising;
    a shared storage device capable of being set on each master unit and adapted to contain data on registered channels which correspond to all of channels used by said master units; and
    a plurality of groups of means incorporated in each said master unit,
    each of said groups of means including,
        setting means for manually setting channels which are to be used by the corresponding master unit and the channels which are not to be used by said corresponding master unit;
        display means for displaying usable or unusable channels and said channels registered by said corresponding master unit;
        channel data processing means adapted to cause said display means to display as either usable or unusable channels, data on said registered channels by reading from said shared storage said data on said registered channels, said channel data processing means being capable of updating said data on said registered channels contained in said shared storage device using said data regarding said channels used and not used by said corresponding master unit; and
        channel selecting means adapted to select, in accordance with said data on channels to be used, channels through which communication is to be performed.

2. The channel management apparatus according to claim 1 wherein each of said groups of means includes a non-volatile memory for storing data on channels used by said corresponding master unit.

3. The channel management apparatus according to claim 1, wherein said channel data processing means includes a central processing unit.

4. The channel management apparatus according to claim 1, wherein said storage device is a card type storage device.

* * * * *